(12) United States Patent
Brumfield et al.

(10) Patent No.: US 10,653,467 B2
(45) Date of Patent: May 19, 2020

(54) INTRA-OSSEOUS PLATE SYSTEM AND METHOD

(71) Applicant: Treace Medical Concepts, Inc., Ponte Vedra Beach, FL (US)

(72) Inventors: David L. Brumfield, Collierville, TN (US); Paul Dayton, Fort Dodge, IA (US); F. Barry Bays, Collierville, TN (US); Joe W. Ferguson, Ponte Vedra Beach, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 153 days.

(21) Appl. No.: 15/148,774

(22) Filed: May 6, 2016

(65) Prior Publication Data

US 2016/0324555 A1    Nov. 10, 2016

Related U.S. Application Data

(60) Provisional application No. 62/157,561, filed on May 6, 2015.

(51) Int. Cl.
*A61B 17/80* (2006.01)
*A61B 17/68* (2006.01)
(Continued)

(52) U.S. Cl.
CPC ........ *A61B 17/8061* (2013.01); *A61B 17/686* (2013.01); *A61B 17/8014* (2013.01);
(Continued)

(58) Field of Classification Search
CPC ... A61B 17/0642; A61B 17/14; A61B 17/147; A61B 17/1604; A61B 17/56;
(Continued)

(56) References Cited

U.S. PATENT DOCUMENTS 2,133,859 A * 10/1938 Hawley .................. A61B 17/80
606/176
2,614,559 A * 10/1952 Livingston ............. A61B 17/72
606/64
(Continued)

FOREIGN PATENT DOCUMENTS

AU    2009227957 B2    7/2014
CA       2491824 A1    9/2005
(Continued)

OTHER PUBLICATIONS

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.
(Continued)

*Primary Examiner* — Nicholas W Woodall
(74) *Attorney, Agent, or Firm* — Fredrikson & Byron, P.A.

(57) ABSTRACT

An intra-osseous support structure can be used to fixate opposed portions of bone. In some examples, the intra-osseous support structure is positioned in openings formed in adjacent portions of bones. Fasteners are inserted through the bone portions to secure the intra-osseous support structure in the bones. Depending on the application, one or more external bone plates may also be applied to the bone portions. The external bone plate may be in compression while the intra-osseous support structure is in tension under load in situ.

13 Claims, 13 Drawing Sheets

(51) Int. Cl.
*A61B 17/88* (2006.01)
*A61B 17/86* (2006.01)
*A61B 17/064* (2006.01)

(52) U.S. Cl.
CPC ...... *A61B 17/8095* (2013.01); *A61B 17/8872* (2013.01); *A61B 17/0642* (2013.01); *A61B 17/86* (2013.01)

(58) Field of Classification Search
CPC . A61B 2017/564; A61B 17/683; A61B 17/80; A61B 17/8061; A61B 17/8095; A61B 17/84; A61B 17/88
See application file for complete search history.

(56) References Cited

U.S. PATENT DOCUMENTS

| | | | |
|---|---|---|---|
| 2,825,329 A * | 3/1958 | Caesar | A61B 17/80 606/309 |
| 3,709,218 A * | 1/1973 | Halloran | A61B 17/72 606/64 |
| 4,159,716 A | 7/1979 | Borchers | |
| 4,187,840 A | 2/1980 | Watanabe | |
| 4,338,927 A | 7/1982 | Volkov et al. | |
| 4,570,624 A | 2/1986 | Wu | |
| 4,627,425 A | 12/1986 | Reese | |
| 4,628,919 A | 12/1986 | Clybum | |
| 4,757,810 A | 7/1988 | Reese | |
| 4,895,141 A | 1/1990 | Koeneman et al. | |
| 4,952,214 A | 8/1990 | Comparetto | |
| 4,959,065 A * | 9/1990 | Arnett | A61B 17/8085 606/285 |
| 4,978,347 A | 12/1990 | Ilizarov | |
| 4,988,349 A | 1/1991 | Pennig | |
| 5,021,056 A | 6/1991 | Hofmann et al. | |
| 5,112,334 A | 5/1992 | Alchermes et al. | |
| 5,207,676 A | 5/1993 | Canadell et al. | |
| 5,254,119 A | 10/1993 | Schreiber | |
| 5,312,412 A | 5/1994 | Whipple | |
| 5,358,504 A | 10/1994 | Paley et al. | |
| 5,364,402 A | 11/1994 | Mumme et al. | |
| 5,413,579 A | 5/1995 | Tom Du Toit | |
| 5,417,694 A | 5/1995 | Marik et al. | |
| 5,439,381 A * | 8/1995 | Cohen | A61C 8/001 433/173 |
| 5,449,360 A | 9/1995 | Schreiber | |
| 5,529,075 A | 6/1996 | Clark | |
| 5,620,442 A | 4/1997 | Bailey et al. | |
| H001706 H | 1/1998 | Mason | |
| 5,788,695 A | 8/1998 | Richardson | |
| 5,803,924 A | 9/1998 | Oni et al. | |
| 5,810,822 A | 9/1998 | Mortier | |
| 5,893,553 A | 4/1999 | Pinkous | |
| 5,935,128 A | 8/1999 | Carter et al. | |
| 5,941,877 A | 8/1999 | Viegas et al. | |
| 5,951,556 A | 9/1999 | Faccioli et al. | |
| 6,030,391 A | 2/2000 | Brainard et al. | |
| 6,162,223 A | 12/2000 | Orsak et al. | |
| 6,171,309 B1 | 1/2001 | Huebner | |
| 6,719,773 B1 | 4/2004 | Boucher et al. | |
| 6,743,233 B1 | 6/2004 | Baldwin et al. | |
| 7,001,388 B2 * | 2/2006 | Orbay | A61B 17/8061 606/286 |
| 7,033,361 B2 | 4/2006 | Collazo | |
| 7,037,342 B2 * | 5/2006 | Nilsson | A61L 27/58 623/18.11 |
| 7,182,766 B1 | 2/2007 | Mogul | |
| 7,241,298 B2 | 7/2007 | Nemec et al. | |
| 7,377,924 B2 | 5/2008 | Raistrick et al. | |
| 7,465,303 B2 | 12/2008 | Riccione et al. | |
| 7,641,660 B2 | 1/2010 | Lakin et al. | |
| D610,257 S | 2/2010 | Horton | |
| 7,686,811 B2 | 3/2010 | Byrd et al. | |
| D629,900 S | 12/2010 | Fisher | |
| 7,972,338 B2 | 7/2011 | O'Brien | |
| D646,389 S | 10/2011 | Claypool et al. | |
| 8,057,478 B2 | 11/2011 | Kuczynski et al. | |
| D651,315 S | 12/2011 | Bertoni et al. | |
| D651,316 S | 12/2011 | May et al. | |
| 8,080,010 B2 | 12/2011 | Schulz et al. | |
| 8,123,753 B2 | 2/2012 | Poncet | |
| 8,137,406 B2 | 3/2012 | Novak et al. | |
| 8,147,530 B2 | 4/2012 | Strnad et al. | |
| 8,167,918 B2 | 5/2012 | Strnad et al. | |
| 8,172,848 B2 | 5/2012 | Tomko et al. | |
| 8,192,441 B2 | 6/2012 | Collazo | |
| 8,197,487 B2 | 6/2012 | Poncet et al. | |
| 8,231,623 B1 | 7/2012 | Jordan | |
| 8,231,663 B2 | 7/2012 | Kay et al. | |
| 8,246,561 B1 | 8/2012 | Agee et al. | |
| D666,721 S | 9/2012 | Wright et al. | |
| 8,262,664 B2 | 9/2012 | Justin et al. | |
| 8,282,644 B2 | 10/2012 | Edwards | |
| 8,282,645 B2 | 10/2012 | Lawrence et al. | |
| 8,292,966 B2 | 10/2012 | Morton | |
| 8,313,492 B2 | 11/2012 | Wong et al. | |
| 8,323,289 B2 | 12/2012 | Re | |
| 8,337,503 B2 | 12/2012 | Lian | |
| 8,343,159 B2 | 1/2013 | Bennett | |
| 8,377,105 B2 | 2/2013 | Bscher | |
| D679,395 S | 4/2013 | Wright et al. | |
| 8,435,246 B2 | 5/2013 | Fisher et al. | |
| 8,475,462 B2 | 7/2013 | Thomas et al. | |
| 8,523,870 B2 | 9/2013 | Green, II et al. | |
| D694,884 S | 12/2013 | Mooradian et al. | |
| D695,402 S | 12/2013 | Dacosta et al. | |
| 8,652,142 B2 | 2/2014 | Geissler | |
| D701,303 S | 3/2014 | Cook | |
| 8,672,945 B2 | 3/2014 | Lavallee et al. | |
| 8,696,716 B2 | 4/2014 | Kartalian et al. | |
| D705,929 S | 5/2014 | Frey | |
| 8,715,363 B2 | 5/2014 | Ratron et al. | |
| 8,728,084 B2 | 5/2014 | Berelsman et al. | |
| 8,758,354 B2 | 6/2014 | Habegger et al. | |
| 8,764,763 B2 | 7/2014 | Wong et al. | |
| 8,771,279 B2 | 7/2014 | Philippon et al. | |
| 8,784,427 B2 | 7/2014 | Fallin et al. | |
| 8,784,457 B2 | 7/2014 | Graham | |
| 8,795,286 B2 | 8/2014 | Sand et al. | |
| 8,801,727 B2 | 8/2014 | Chan et al. | |
| 8,808,303 B2 | 8/2014 | Stemniski et al. | |
| 8,828,012 B2 | 9/2014 | May et al. | |
| 8,858,602 B2 | 10/2014 | Weiner et al. | |
| 8,882,778 B2 | 11/2014 | Ranft | |
| 8,911,482 B2 * | 12/2014 | Lee | A61B 17/8057 606/286 |
| 8,998,903 B2 | 4/2015 | Price et al. | |
| 8,998,904 B2 | 4/2015 | Zeetser et al. | |
| 9,023,052 B2 | 5/2015 | Lietz et al. | |
| 9,044,250 B2 | 6/2015 | Olsen et al. | |
| 9,060,822 B2 | 6/2015 | Lewis et al. | |
| 9,089,376 B2 | 7/2015 | Medoff et al. | |
| 9,101,421 B2 | 8/2015 | Blacklidge | |
| 9,107,715 B2 | 8/2015 | Blitz et al. | |
| D765,844 S | 9/2016 | DaCosta | |
| D766,434 S | 9/2016 | DaCosta | |
| D766,437 S | 9/2016 | DaCosta | |
| D766,438 S | 9/2016 | DaCosta | |
| D766,439 S | 9/2016 | DaCosta | |
| 9,750,538 B2 | 9/2017 | Soffiatti et al. | |
| 2002/0099381 A1 | 7/2002 | Maroney | |
| 2002/0107519 A1 | 8/2002 | Dixon et al. | |
| 2002/0198531 A1 | 12/2002 | Millard et al. | |
| 2003/0135212 A1 * | 7/2003 | Y. Chow | A61B 17/72 606/64 |
| 2004/0010259 A1 | 1/2004 | Keller et al. | |
| 2004/0039394 A1 | 2/2004 | Conti et al. | |
| 2004/0097946 A1 | 5/2004 | Dietzel et al. | |
| 2005/0004676 A1 | 1/2005 | Schon et al. | |
| 2005/0075641 A1 | 4/2005 | Singhatat et al. | |
| 2005/0101961 A1 | 5/2005 | Huebner et al. | |
| 2005/0149042 A1 | 7/2005 | Metzger | |
| 2005/0228389 A1 | 10/2005 | Stiernborg | |

(56) References Cited

U.S. PATENT DOCUMENTS

| | | |
|---|---|---|
| 2005/0273112 A1 | 12/2005 | McNamara |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0091197 A1 | 4/2008 | Coughlin |
| 2008/0140081 A1 | 6/2008 | Heavener et al. |
| 2008/0172054 A1 | 7/2008 | Claypool et al. |
| 2008/0208252 A1 | 8/2008 | Holmes |
| 2008/0262500 A1 | 10/2008 | Collazo |
| 2008/0269908 A1 | 10/2008 | Warburton |
| 2009/0036893 A1 | 2/2009 | Kartalian et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Lvalch et al. |
| 2009/0312802 A1* | 12/2009 | DaSilva ............... A61B 17/683 606/304 |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0324556 A1 | 12/2010 | Tyber et al. |
| 2011/0087295 A1 | 4/2011 | Kubiak et al. |
| 2011/0093084 A1 | 4/2011 | Morton |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130383 A1 | 5/2012 | Budoff |
| 2012/0184961 A1 | 7/2012 | Johannaber |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0096563 A1 | 4/2013 | Meade et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0194884 A1 | 7/2014 | Martin et al. |
| 2014/0207144 A1 | 7/2014 | Lee et al. |
| 2014/0214037 A1* | 7/2014 | Mayer ............... A61B 17/0642 606/75 |
| 2014/0249537 A1 | 9/2014 | Wong et al. |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2015/0032168 A1 | 1/2015 | Drsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton et al. |
| 2016/0022315 A1 | 1/2016 | Soffiatti et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0354127 A1 | 12/2016 | Lundquist et al. |
| 2017/0042599 A1 | 2/2017 | Bays et al. |
| 2017/0079669 A1 | 3/2017 | Bays et al. |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |

(56) References Cited

FOREIGN PATENT DOCUMENTS

| | | |
|---|---|---|
| CN | 204446081 U | 7/2015 |
| EP | 685206 B1 | 9/2000 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| FR | 2362616 A1 | 3/1978 |
| FR | 2764183 B1 | 11/1999 |
| FR | 3030221 A1 | 6/2016 |
| GB | 2154143 A | 9/1985 |
| GB | 2154144 A | 9/1985 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |
| WO | 0166022 A1 | 9/2001 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015105880 A1 | 7/2015 |
| WO | 2015127515 A2 | 9/2015 |

OTHER PUBLICATIONS

Anderson et al., "Uncemented Star Total Ankle Prostheses," The Journal of Bone and Joint Surgery, vol. 86(1, Suppl 2), Sep. 2004, pp. 103-111, (Abstract Only).

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Garthwait, "Accu-Cut System Facilitates Enhanced Precision," Podiatry Today, vol. 18, No. 6, Jun. 2005, 6 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).

"HAT-TRICK Lesser Toe Repair System," Smith & Nephew, Brochure, Aug. 2014, 12 pages.

"Hoffmann II Compact External Fixation System," Stryker, Brochure, Literature No. 5075-1-500, 2006, 12 pages.

"Hoffmann II Micro Lengthener," Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

"Lag Screw Target Bow," Stryker Leibinger GmbH & Co. KG, Germany 2004, 8 pages.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Michelangelo Bunion System, Surgical Technique, Instratek Incorporated, publication date unknown, 4 pages.

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect of Ankle Flexion Angle on Axial Alignment of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

(56) References Cited

OTHER PUBLICATIONS

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Rx-Fix Mini Rail External Fixator, Wright Medical Technology, Brochure, Aug. 15, 2014, 2 pages.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.
Siddiqui et al. "Fixation of Metatarsal Fracture With Bone Plate in A Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Small Bone External Fixation System, Acumed, Surgical Technique, Effective date Sep. 2014, 8 pages.
Stableloc External Fixation System, Acumed, Product Overview, Effective date Sep. 2015, 4 pages.
Stahl et al., "Derotation of Post-Traumatic Femoral Deformities by Closed Intramedullary Sawing," Injury, vol. 37, No. 2, Feb. 2006, pp. 145-151, (Abstract Only).
Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Weber et al., "A Simple System for Navigation of Bone Alignment Osteotomies of The Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.

* cited by examiner

INTRA-OSSEOUS PLATE SYSTEM AND METHOD

RELATED APPLICATION

This application claims the benefit of US Provisional Application Ser. No. 62/157,561, filed May 6, 2015, the entire contents of which are incorporated herein by reference.

TECHNICAL FIELD

This disclosure relates generally to bone plate devices and methods for fixing bone using plate devices.

BACKGROUND

Bones, such as the bones of a foot, may be anatomically misaligned. In certain circumstances, surgical intervention is required to correctly align the bones to reduce patient discomfort and improve patient quality of life. Surgical intervention may involve cutting one or more of the misaligned bones and then physically realigning the bones into an anatomically corrected position. A bone plate or multiple bone plates may be used to hold the bones in the anatomically corrected position, helping to prevent the bones from shifting back to their misaligned position.

SUMMARY

In general, this disclosure is directed to bone fixation systems and techniques for fixating bones. In some examples, a bone plating system includes an intra-osseous support structure configured to be placed in an opening formed between adjacent bones. For example, during a tarsal-metatarsal fusion procedure in which a first metatarsal is realigned with respect to a second metatarsal, the intra-osseous support structure may be placed within the osseous tissue of the first metatarsal and the medial cuneiform, spanning the tarsal-metatarsal joint. An opening or groove may be formed in the end of the first metatarsal facing the medial cuneiform and also in the end of the medial cuneiform facing the first metatarsal, providing cavities in which opposed ends of the intra-osseous support structure are inserted. One or more fasteners can be used to secure the intra-osseous support structure to the bones in which the fastener is inserted. For instance, in the example of a tarsal-metatarsal fusion procedure, a fastener may be inserted into the medial cuneiform (e.g., from the dorsal toward the plantar side), securing the intra-osseous support structure to the medial cuneiform. A second fastener can be inserted into the first metatarsal (e.g., from the dorsal toward the plantar side), securing the intra-osseous support structure to the first metatarsal.

In some applications, a bone plate is also applied on exterior surfaces of the bone portions into which the intra-osseous support structure is inserted. For example, one or more flat or curved bone plates may be applied to exterior surfaces of bone portions containing the intra-osseous support structure. Depending on the configuration, the exterior bone plate(s) may be in compression while the intra-osseous support structure is in tensions under load, providing a balanced fixation system to effectively fixation opposed portions of bone.

In one example, a bone plating system is described that includes a fastener having a length and an intra-osseous support structure. The example specifies that the intra-osseous support structure is configured to be placed in an opening formed in a first bone portion and a second bone portion and has an aperture to receive the fastener.

In another example, a method of plating a bone is described. The method includes forming an opening in a first bone portion and a second bone portion and placing an intra-osseous support structure in the opening. The method further includes inserting a first fastener through the first bone portion and into the intra-osseous support structure and inserting a second fastener through the second bone portion and into the intra-osseous support structure.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Embodiments of the invention include a bone plating system. Embodiments of the system can be useful for providing structural support to bones subject to a surgical procedure, such as a bone alignment, osteotomy, fracture repair, and/or fusion procedure. Such a procedure may be performed, for example, on bones (e.g., adjacent bones separated by a joint or different portions of a single bone separated by a fracture) in the foot or hand. In one example, the procedure can be performed to correct an alignment between a metatarsal (e.g., a first metatarsal) and a cuneiform (e.g., a first cuneiform), such as a bunion correction. An example of such a procedure is a lapidus procedure. In another example, the procedure can be performed by modifying an alignment of a metatarsal (e.g., a first metatarsal). An example of such a procedure is a basilar metatarsal osteotomy procedure.

Figure 1:
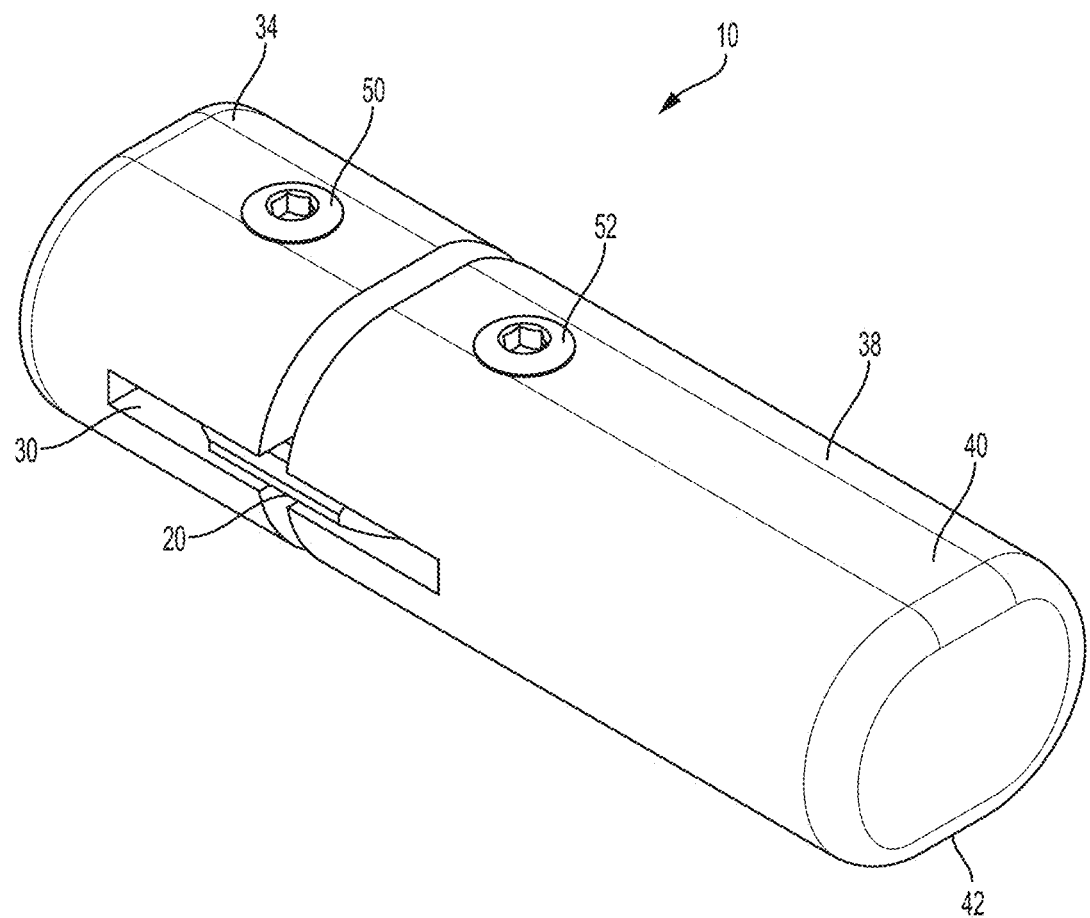
FIG. 1 is a perspective view of a bone plating system in accordance with an embodiment of the invention.

As shown in FIG. 1, embodiments of the bone plating system 10 include an intra-osseous support structure 20. As shown, the intra-osseous support structure can be adapted to be positioned intra-osseously. In such embodiments, the intra-osseous support structure is positioned within a thickness of a bone, such that both of its major surfaces face bone (e.g., cancellous bone). In the embodiment shown, the intra-osseous support structure 20 is adapted to be positioned within an opening 30 of a first bone portion 34 and a second bone portion 38, the opening leading to a cavity or void within the respective bone portions. As shown, in a bone portion having a dorsal surface 40 and a plantar surface 42, the opening can be formed closer to the plantar surface than the dorsal surface (e.g., between about one-half and two-thirds through the thickness of the bone). In certain embodiments, the opening crosses a centerline of one or both bone portions. In such embodiments, the bone defining the opening, and the intra-osseous support structure placed therein, will be in tension under load in situ. Such an intra-osseous support structure can be useful for providing structural support to bones subject to a surgical procedure.

The intra-osseous support structure 20 can include any useful form. In some embodiments, the intra-osseous support structure has a first major surface, a second major surface, and a perimeter edge extending between the first major surface and the second major surface. In the embodiment shown in FIG. 1, the intra-osseous support structure is generally planar as are its first and second major surfaces. The major surfaces can be devoid of any protrusions. In certain embodiments, one or both of the major surfaces can include a surface treatment such as a texture. In some embodiments (not shown), the intra-osseous support structure can include a portion generally perpendicular to a first major surface. For example, the intra-osseous support structure can include a portion that extends from a side (e.g., a medial side) and bends or curves in an upward (e.g., dorsal) or a downward (e.g. plantar) direction around and/or in apposition to a cortical surface of a bone.

In the embodiment shown in FIG. 1, the intra-osseous support structure 20 is connected to a bone portion by at least one fastener 50. In some embodiments, the intra-osseous support structure has a first portion for placement in the first bone portion 34 and a second portion for placement in the second bone portion 38, and at least one aperture (not shown in FIG. 1) to receive a respective fastener can be provided on each portion. In situ, the fastener can extend through a bone surface (e.g., a dorsal surface) and a portion of the thickness of a bone to the intra-osseously positioned support structure and be received into an aperture thereof.

Figure 2:
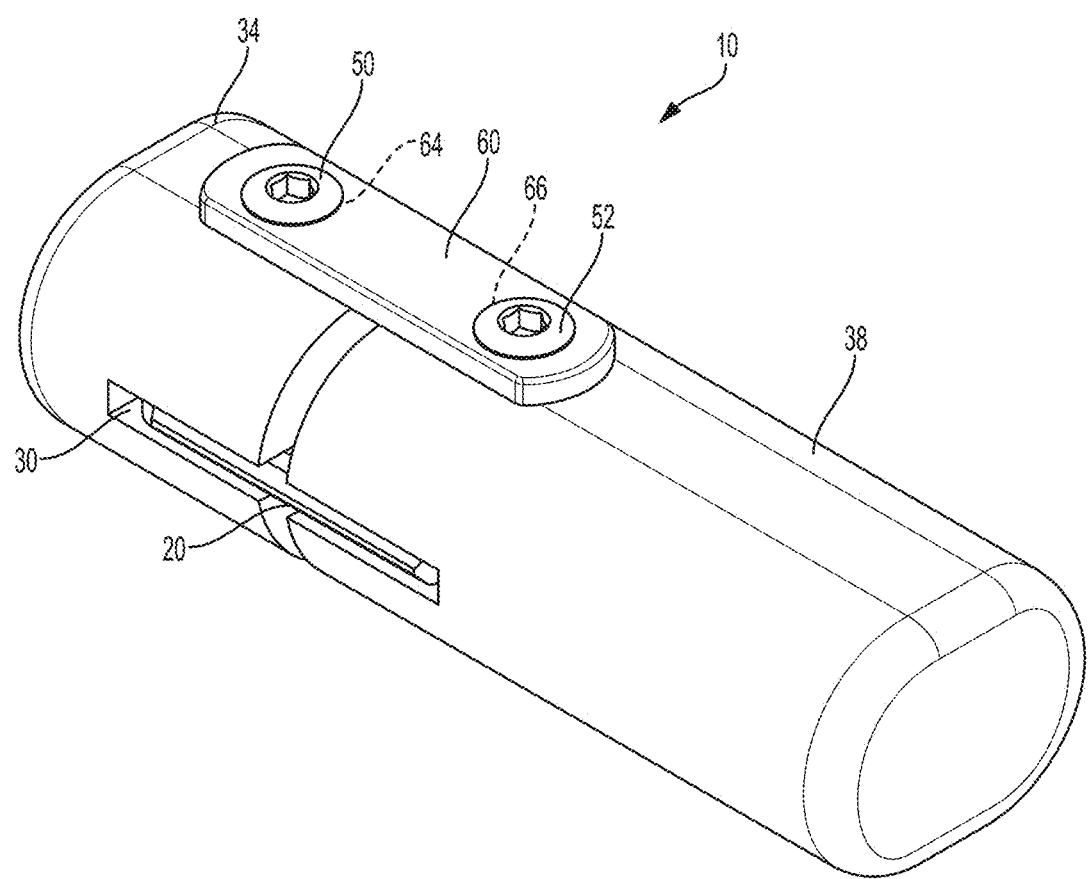
FIG. 2 is a perspective view of a bone plating system in accordance with an embodiment of the invention.
Figure 3:
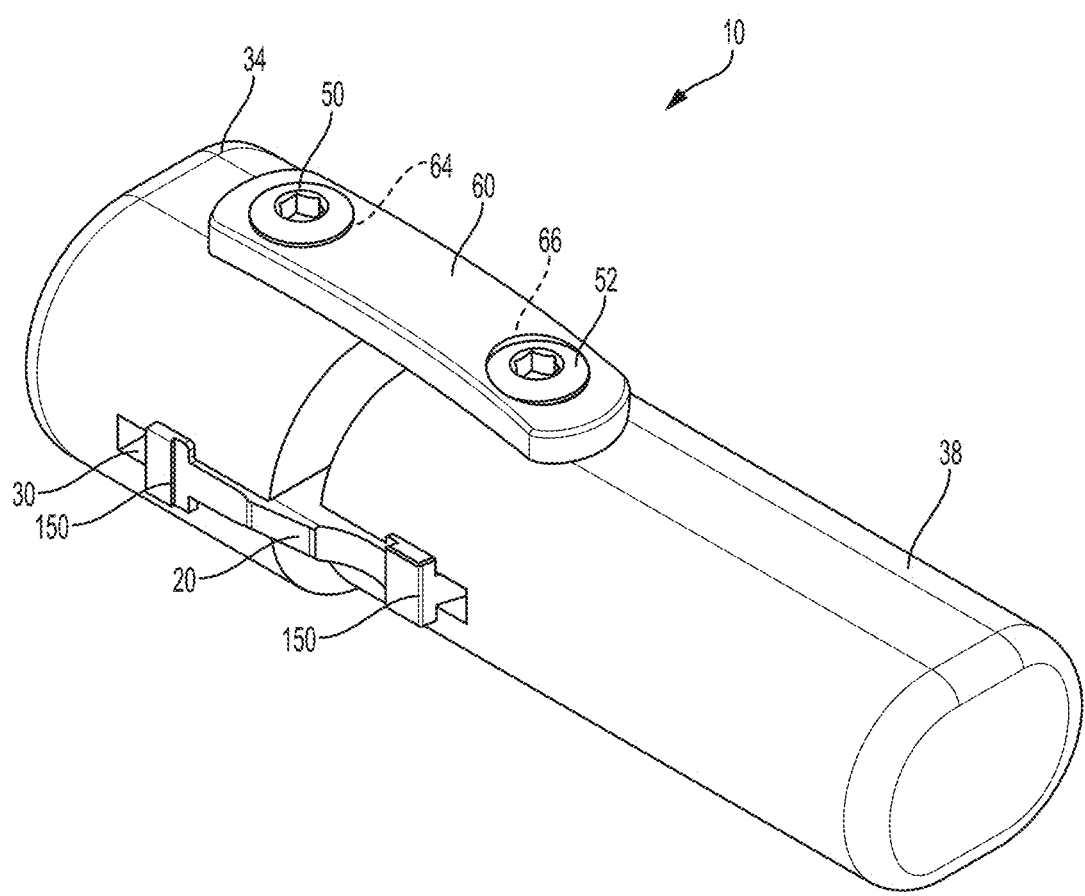
FIG. 3 is a perspective view of a bone plating system in accordance with an embodiment of the invention.

As shown in FIGS. 2 and 3, some embodiments of the bone plating system 10 can include a bone plate 60. In the embodiment shown, the plate is adapted to be positioned on an outer surface of the first bone portion 34 and an outer surface of the second bone portion 38. As shown, in a bone portion having a dorsal surface and a plantar surface, the dorsal surface, and the plate placed thereon, will be in compression under load in situ. Accordingly, some embodiments of the plating system include a plate in compression and an intra-osseous support structure in tension under load in situ. Such a plating system can be useful for providing structural support to bones subject to a surgical procedure.

The bone plate 60 can include any suitable form. In some embodiments, the bone plate has a bone facing surface and a surface opposite the bone facing surface. In certain embodiments, such as the embodiment shown in FIG. 2, the bone plate 60 includes a generally planar member having generally planar surfaces. In other embodiments, such as the embodiment shown in FIG. 3, the bone plate 60 includes a curved shape (about and/or along its longitudinal axis). For example, the surface facing the bone can be concave and the opposite surface can be convex. In certain embodiments, the surface of the bone plate facing the bone may also have at least one protrusion to engage with the surface of the bone.

In embodiments of the plating system having a plate 60, the plate and intra-osseous support structure 20 can be connected to the bone and each other by the at least one fastener 50. In such embodiments, the bone plate 60 can have at least one aperture 64, 66 to receive respective fasteners 50, 52. In the embodiment shown, the bone plate has a first portion for placement on the first bone portion 34 and a second portion for placement on the second bone portion 38. At least one aperture 64, 66 for receiving a respective fastener 50, 52 can be provided on each portion. Further, the intra-osseous support structure 20 can have at least one aperture (not shown in FIGS. 2 and 3) aligned to receive the respective fastener. In situ, the fastener can extend through the bone plate, a surface of the bone, and a portion of the thickness of a bone to the intra-osseously positioned support structure and be received into the aperture thereof. After final placement, in some embodiments, the bone plate and intra-osseous support structure will be generally parallel to each other.

In some embodiments, the aperture in the intra-osseous support structure can include an attachment mechanism configured to engage a fastener. The fastener and attachment mechanism can include any structure suitable for engagement. In some embodiments, the fastener includes a screw, and the attachment mechanism includes a threaded aperture to receive and engage the screw. The attachment mechanism can include guides to facilitate alignment with the fasteners. In some embodiments, the fastener has a length that is less than the thickness of the bone. In certain embodiments, the fastener will have a length between about one-half of the thickness of the bone and the entire thickness of the bone. For example, the fastener can have a length of about two-thirds the thickness of the bone. In some embodiments, the fastener can extend through the aperture of the intra-osseous support structure (optionally engaging an attachment member thereof) and engage bone on one or both sides of the intra-osseous support structure.

Figure 4:
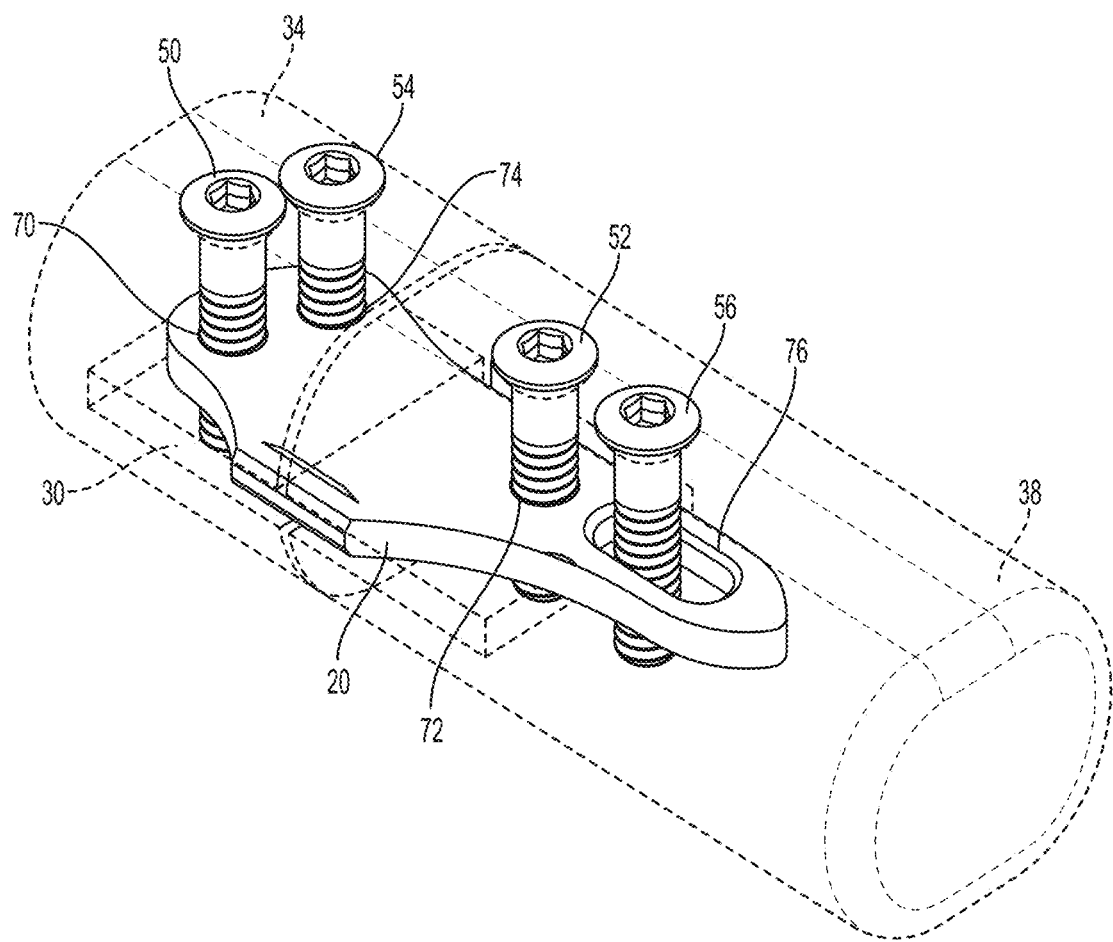
FIG. 4 is a perspective view of a bone plating system in accordance with an embodiment of the invention, with bone portions depicted as transparent.
Figure 5:
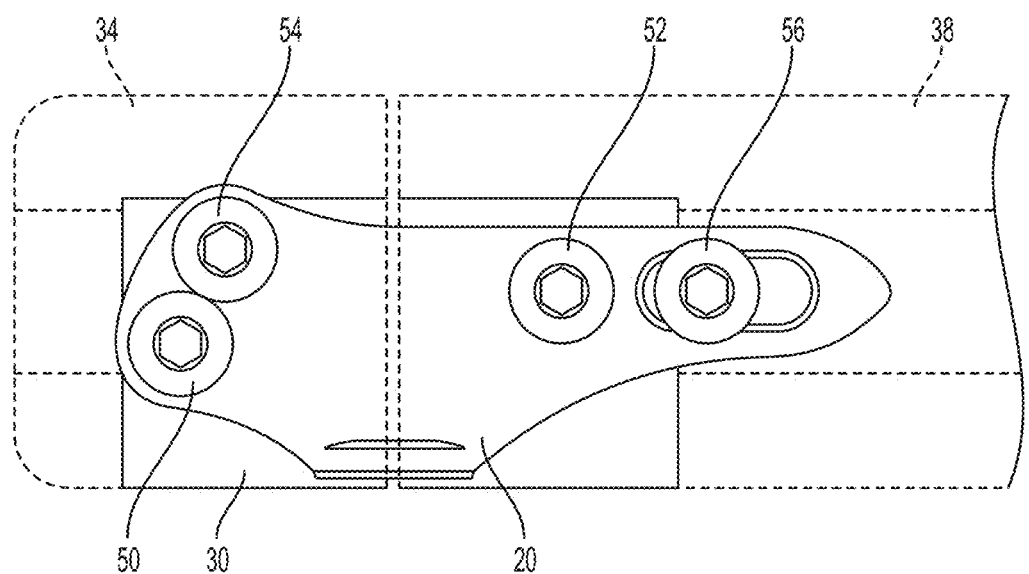
FIG. 5 is a top view of a bone plating system in accordance with an embodiment of the invention, with bone portions depicted as transparent.

Any number of fasteners and respective intra-osseous support structure apertures can be provided. In the embodiment shown in FIGS. 1-3, the intra-osseous support structure 20 includes two apertures to receive two respective fasteners 50, 52. In the embodiment shown in FIGS. 4 and 5, the intra-osseous support structure 20 includes four apertures 70, 72, 74, 76 to receive four respective fasteners 50, 52, 54, 56. In other embodiments, the intra-osseous support structure includes three apertures to receive three respective fasteners. In an embodiment of an intra-osseous support structure having a portion generally perpendicular to a first major surface, such a portion may include one or more apertures for receiving a fastener.

Figure 6:
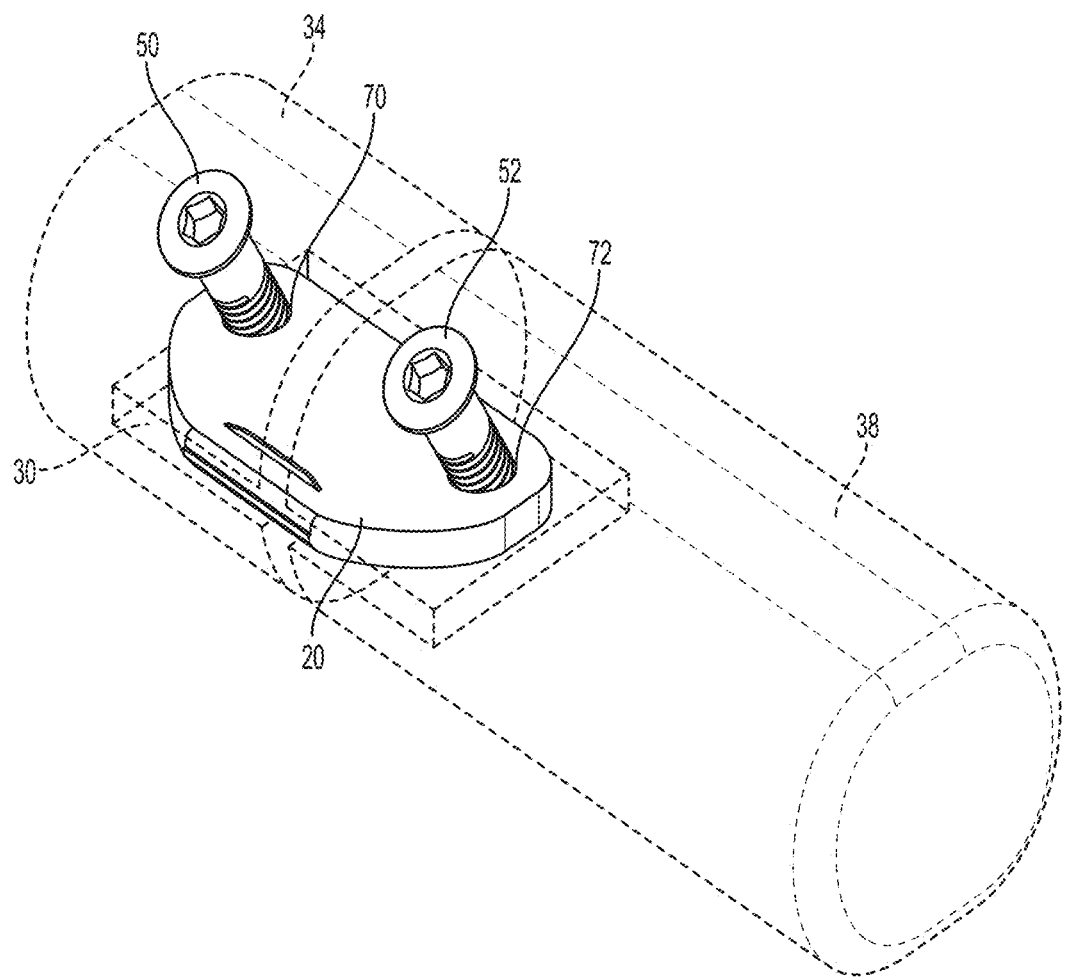
FIG. 6 is a perspective view of a bone plating system in accordance with an embodiment of the invention, with bone portions depicted as transparent.
Figure 7:
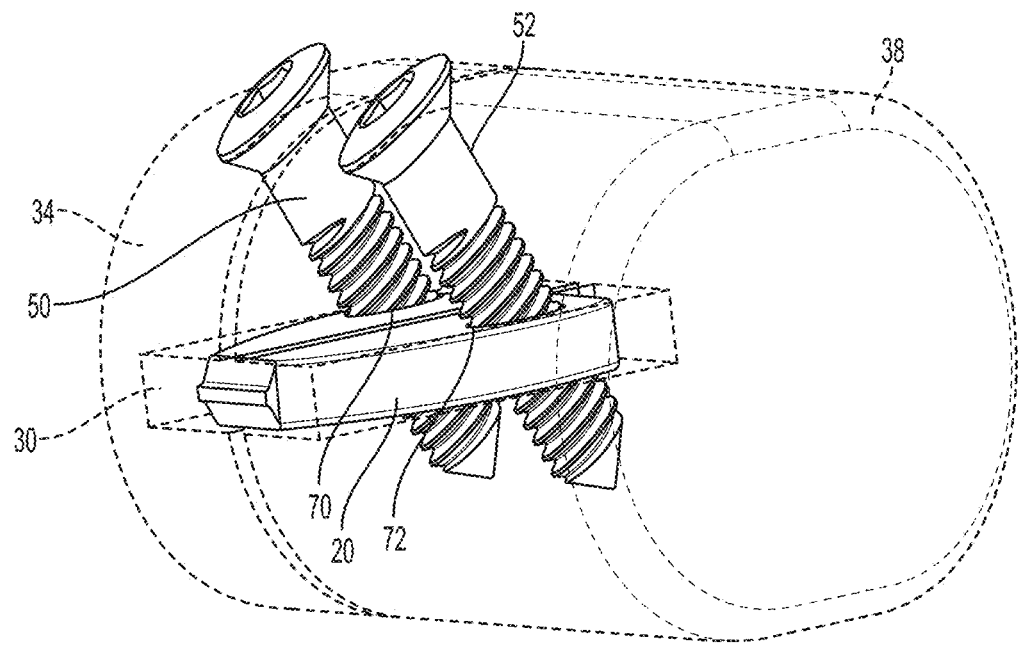
FIG. 7 is a perspective view of a bone plating system in accordance with an embodiment of the invention, with bone portions depicted as transparent.
Figure 8:
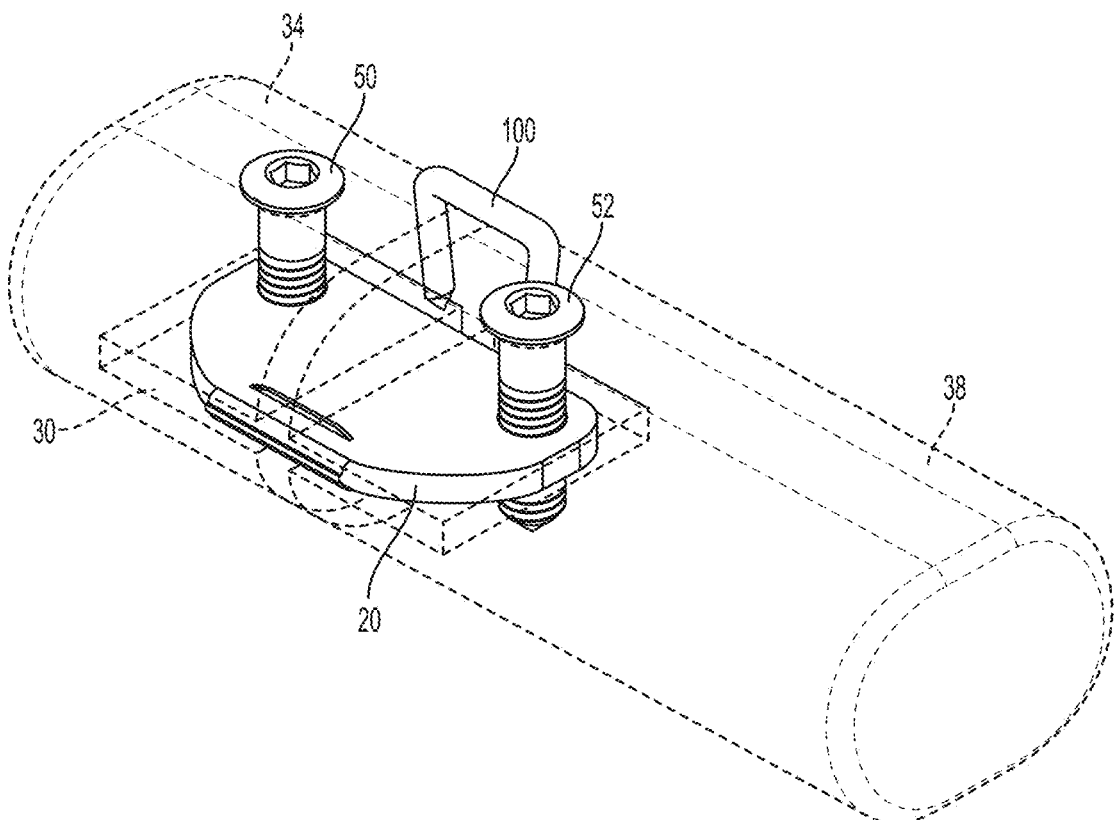
FIG. 8 is a perspective view of a bone plating system in accordance with an embodiment of the invention, with bone portions depicted as transparent.
Figure 9:
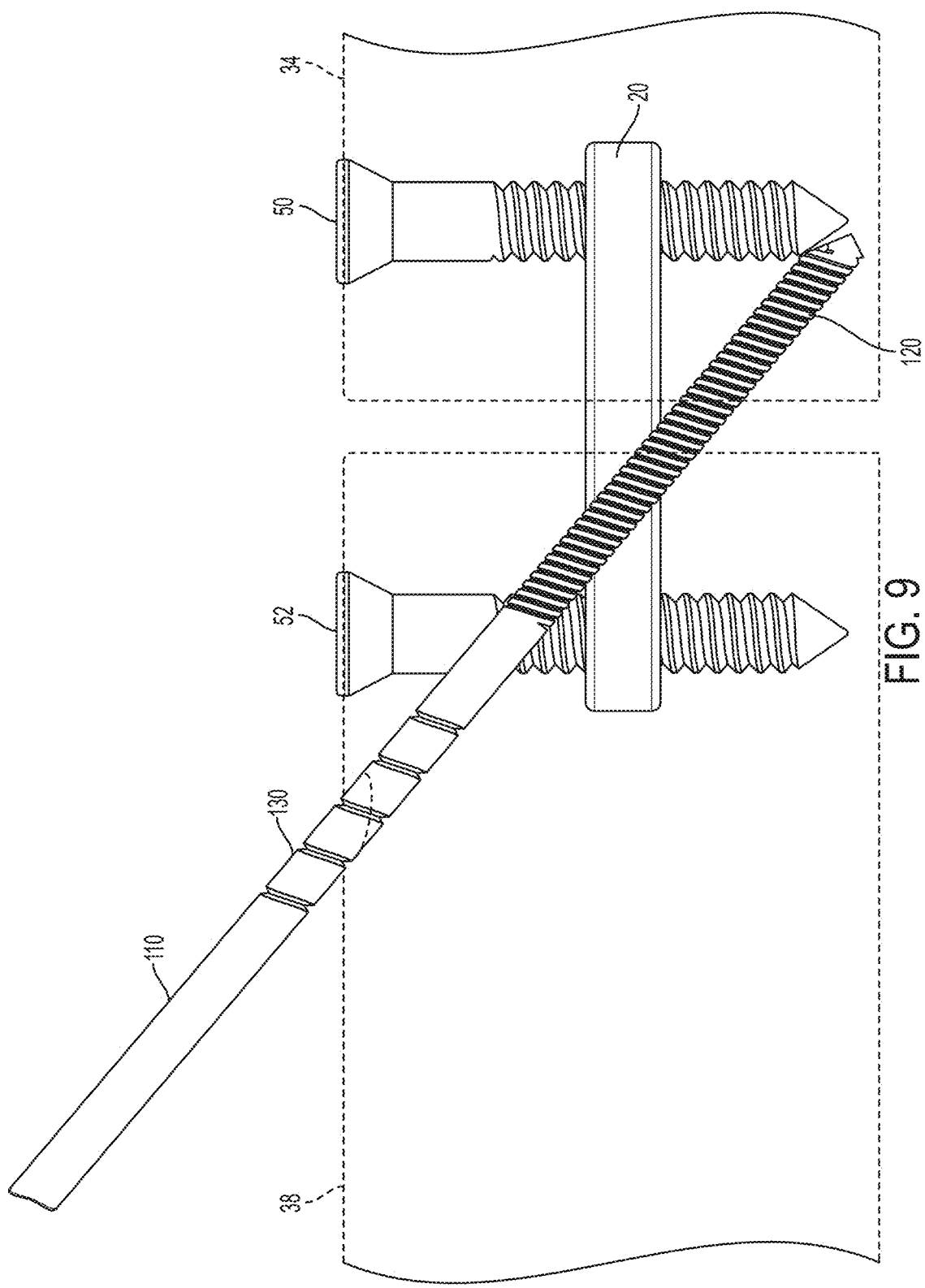
FIG. 9 is a side view of a bone plating system in accordance with an embodiment of the invention, with bone portions depicted as transparent.
Figure 10:
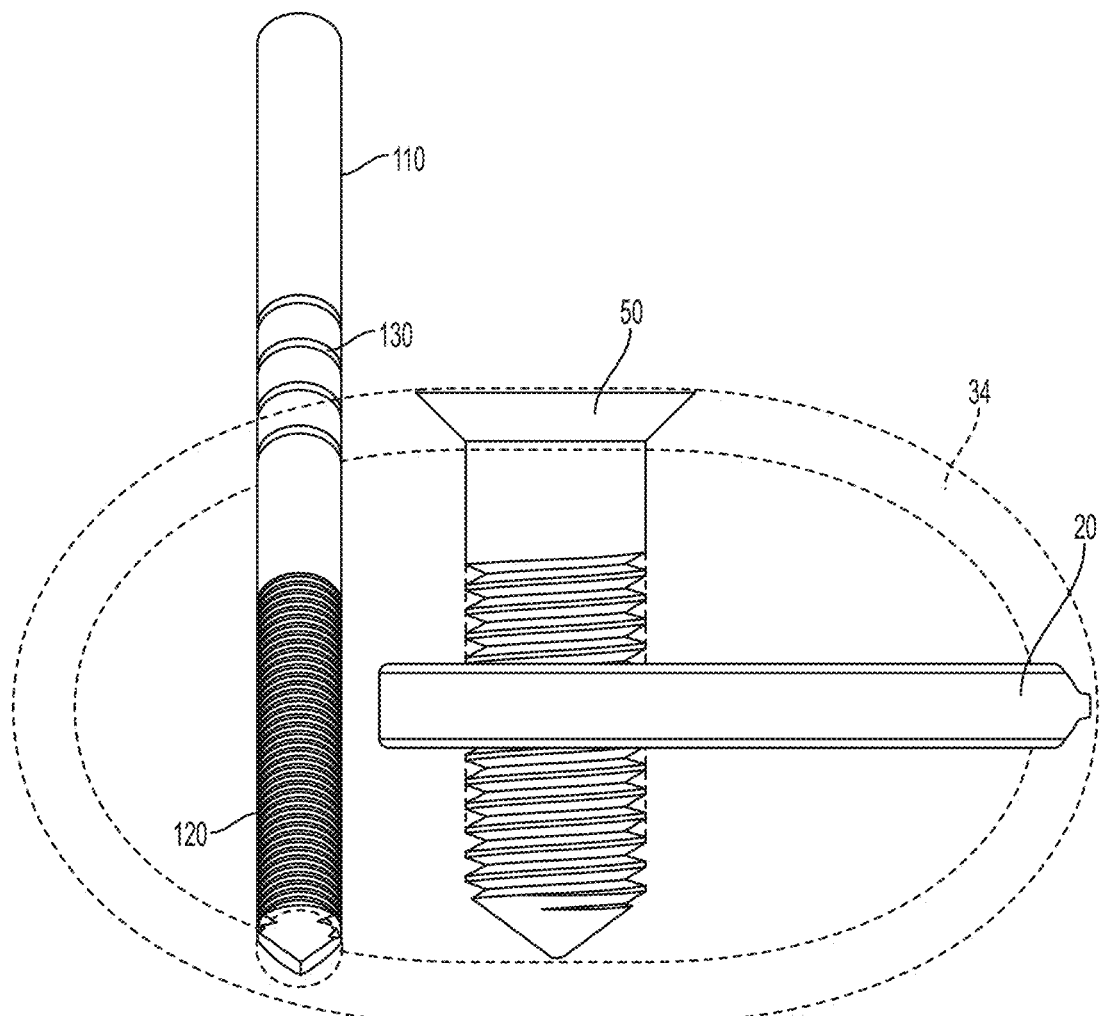
FIG. 10 is an end view of a bone plating system in accordance with an embodiment of the invention, with bone portions depicted as transparent.
Figure 11:
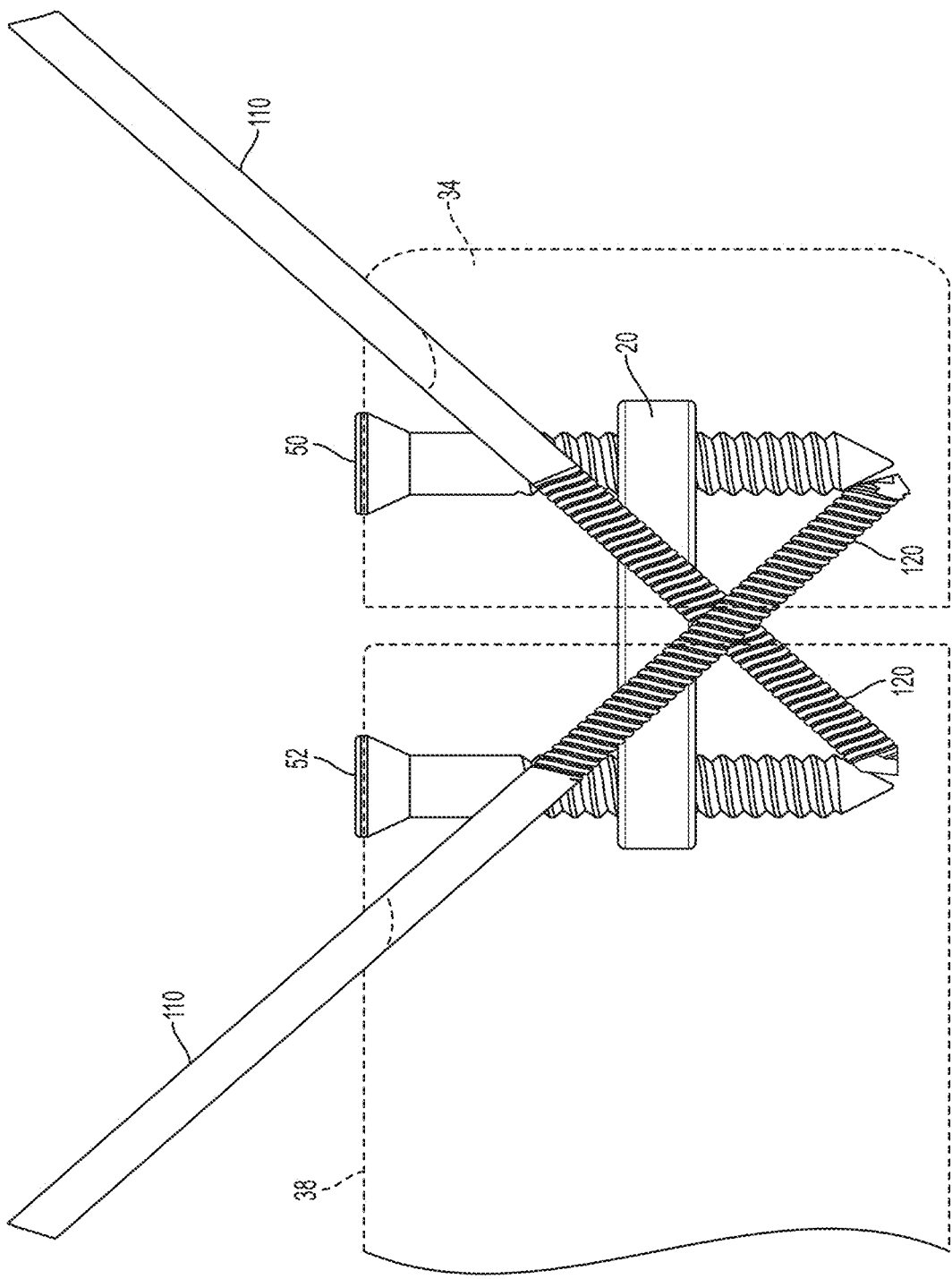
FIG. 11 is a side view of a bone plating system in accordance with an embodiment of the invention, with bone portions depicted as transparent.
Figure 12:
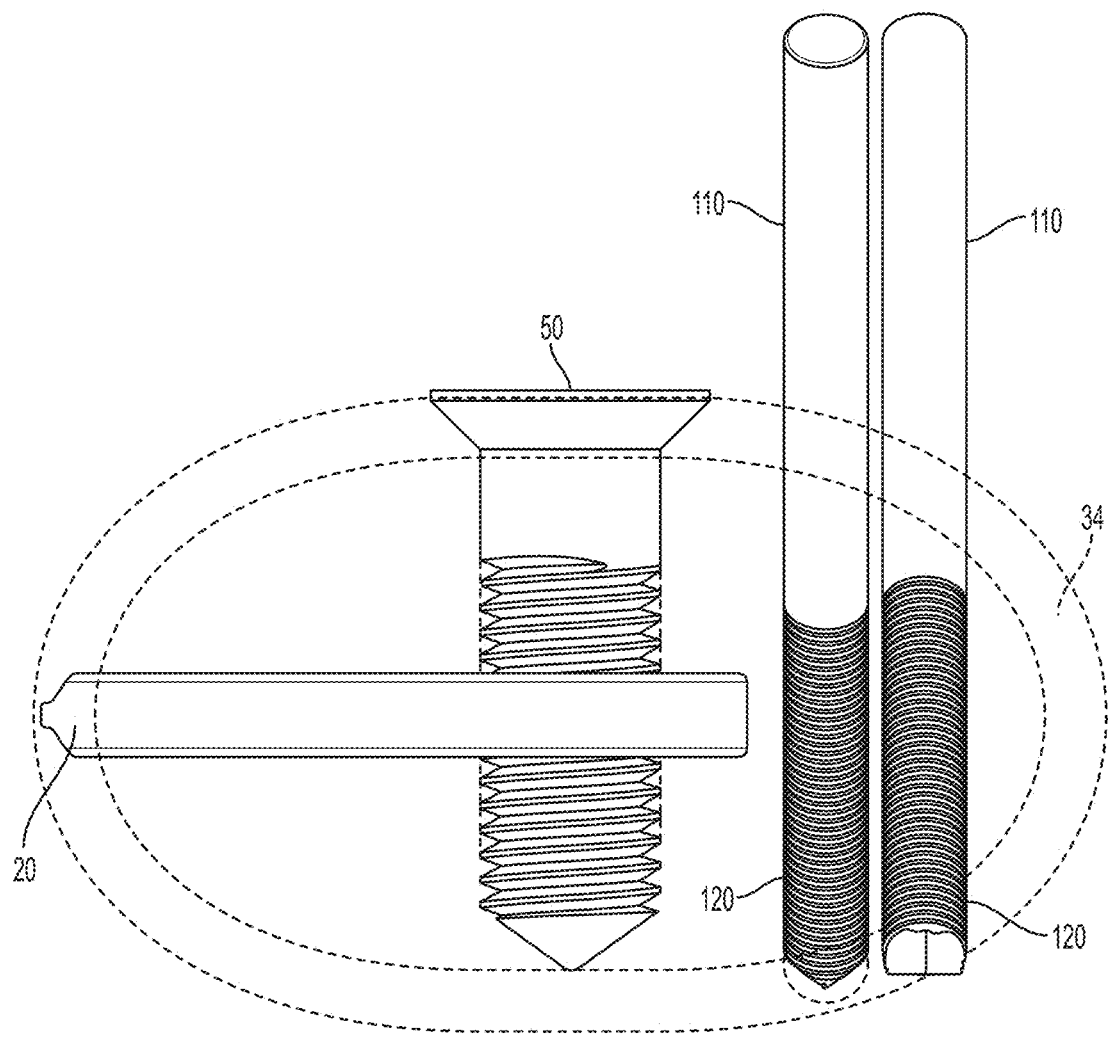
FIG. 12 is an end view of a bone plating system in accordance with an embodiment of the invention, with bone portions depicted as transparent.

The fasteners and respective apertures can be provided in any orientation. In some embodiments, such as the embodiments shown in FIG. 4, the apertures 70, 72, 74, 76 have a longitudinal axis perpendicular to a first major surface of the intra-osseous support structure 20. In other embodiments, such as the embodiment shown in FIGS. 6 and 7, the apertures 70, 72 have a longitudinal axis that intersects a first major surface of the intra-osseous support structure 20 at a skewed angle (e.g., an angle ranging from about 20 degrees to about 40 degrees from perpendicular). Further, in some embodiments, fasteners 50, 52 can extend from the bone surface and through the bone generally parallel to each other. In other embodiments, first and second fasteners can extend from the bone surface and through the bone at a skewed angle relative to each other. In embodiments of the plating system that include a plate, apertures 64, 66 can be configured such that first and second fasteners 50, 52 can extend from the bone plate 60 generally parallel to each other or at a skewed angle relative to each other.

As shown in FIGS. 8-12, some embodiments of the plating system can include an additional support that does not engage the intra-osseous support structure. Such an additional support can be useful for providing rotational stability to the plated bone portions. In the embodiment shown in FIG. 8, the additional support includes a staple 100 having an end in each bone portion 34, 38. In the example shown in FIGS. 9-10, the additional support includes a pin 110 extending across the bone portions 34, 38 at an angle (e.g., about 45 degrees). In the embodiment shown, the pin 110 includes threads 120 on its distal portion to engage bone. It also includes notches 130 on its proximal portion. The pin can be broken at a desired notch after installation. In the embodiment shown in FIGS. 11 and 12, two pins 110 are provided. As shown, the pins are inserted such that they extend across the bone portions 34, 38 in a crossing pattern, each at an angle (e.g., about 45 degrees).

Figure 13:
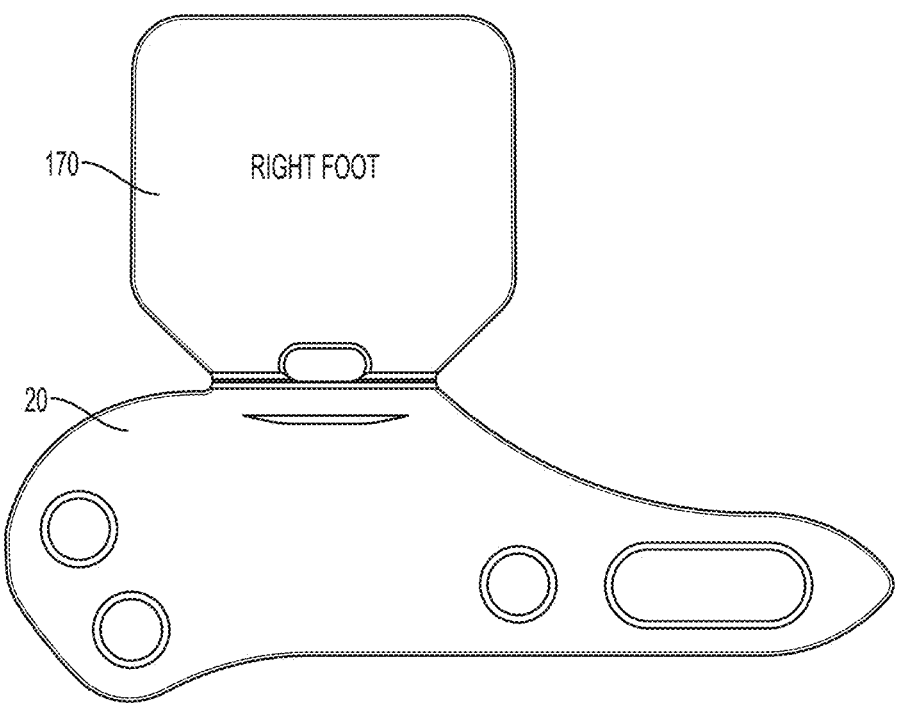
FIG. 13 is a top plan view of an intra-osseous support structure in accordance with an embodiment of the invention.
Figure 14:
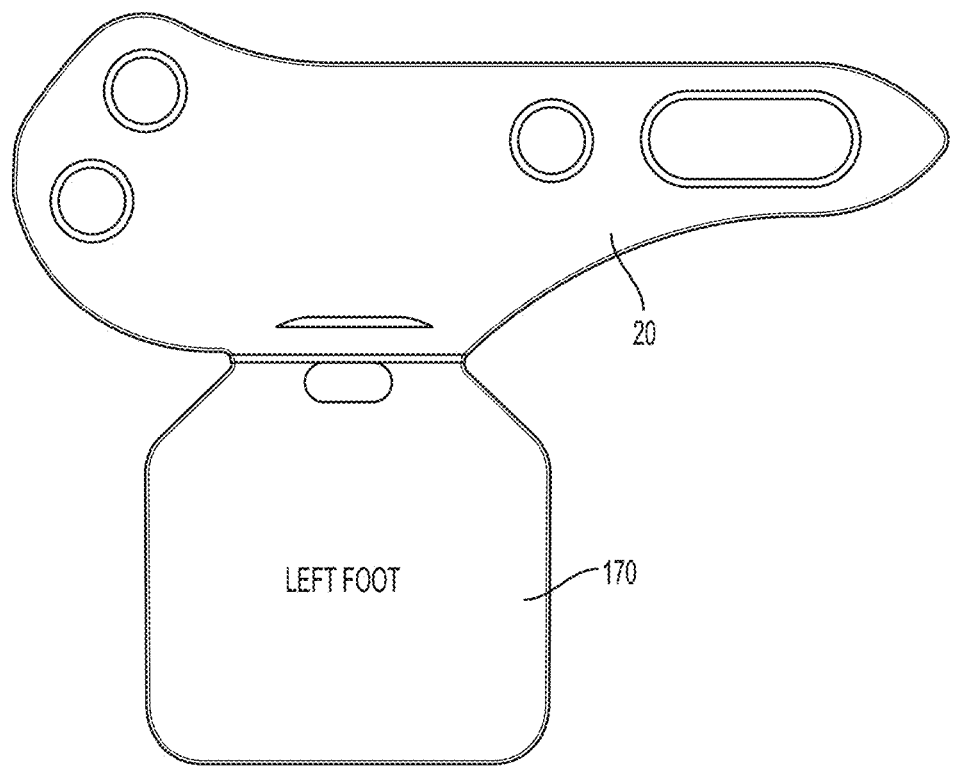
FIG. 14 is a top plan view of an intra-osseous support structure in accordance with an embodiment of the invention.
Figure 15:
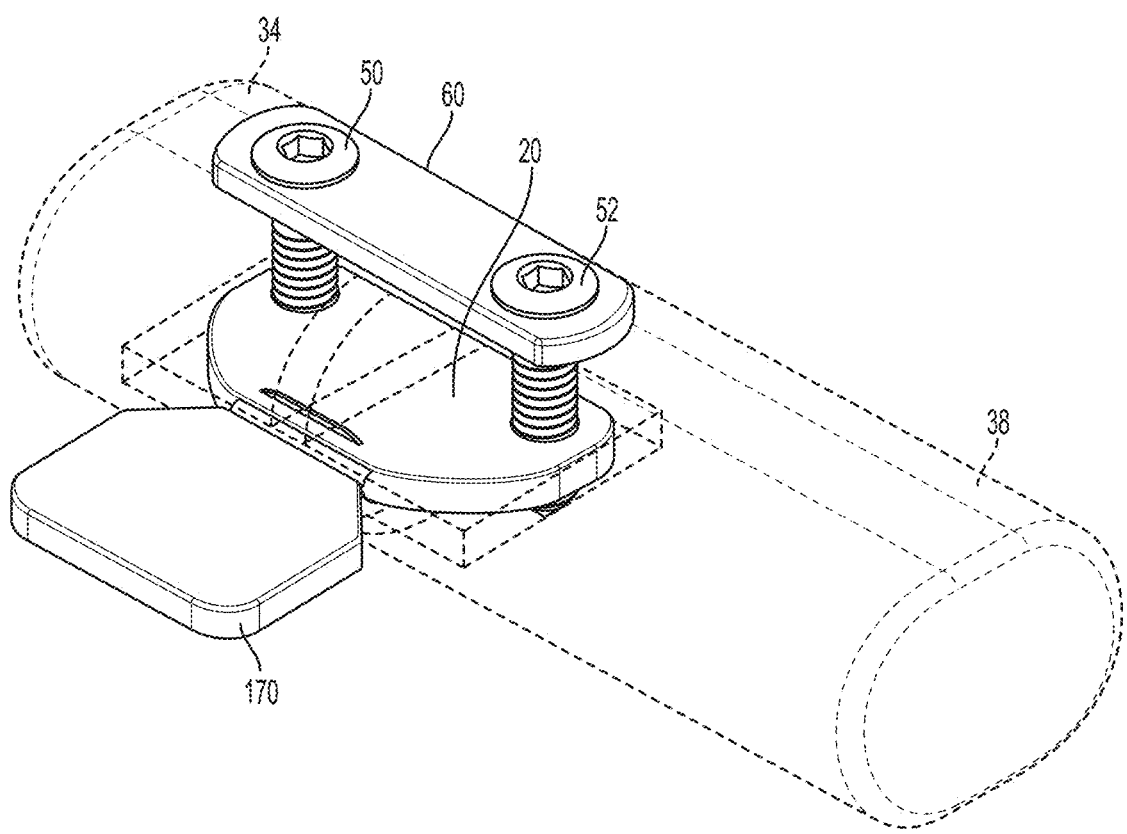
FIG. 15 is a perspective view of a bone plating system in accordance with an embodiment of the invention, with bone portions depicted as transparent.
Figure 16:
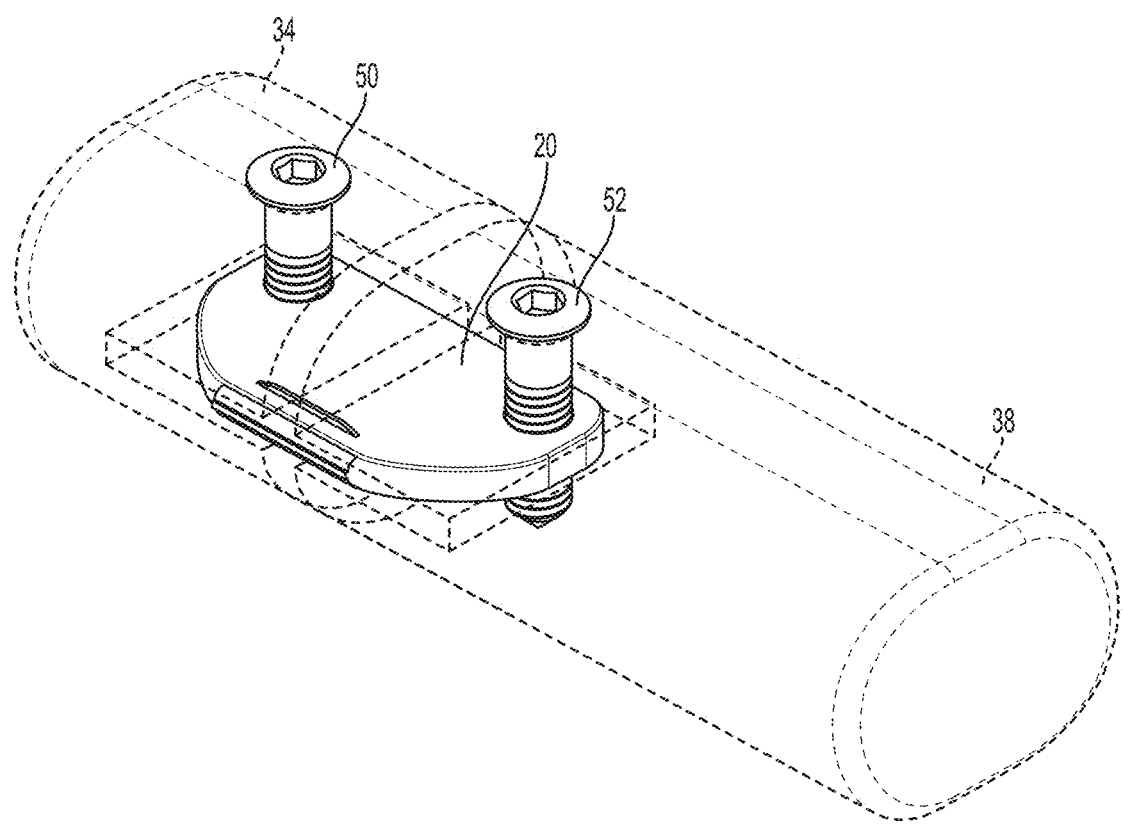
FIG. 16 is a perspective view of a bone plating system in accordance with an embodiment of the invention, with bone portions depicted as transparent.

The plating system can also include features useful for placing the intra-osseous support structure. As shown in FIG. 3, the intra-osseous support structure 20 can include a stop 150 on the perimeter edge that extends past the first major surface or the second major surface. In some embodiments, the stop is on a medial side of the intra-osseous support structure. In other embodiments, as shown in FIGS. 13-15, a tab 170 extending beyond the perimeter edge (e.g., on a medial side) can be provided. The tab can be useful for placing the intra-osseous support structure within the bone, and, in some embodiments, can be provided with break seam such that it can be easily removed from the intra-osseous support structure after placement. FIG. 16 shows in intra-osseous support structure 20 with the tab removed.

The plating system can be used to join any bone portions. In one example, the first bone portion and the second bone portion are portions of a single bone separated by a fracture. As a further example, the first bone portion and the second bone portion are portions of a single bone separated by an osteotomy. As another example, the first bone portion and the second bone portion can be portions of two different bones separated by a joint, such as a cuneiform (e.g., medial cuneiform) and a metatarsal (e.g., first metatarsal). In the two-bone example, the intra-osseous support structure can be placed intra-osseously in the cuneiform and the metatarsal in an opening that spans the joint therebetween (e.g., tarsal-metatarsal joint). In such an embodiment, fasteners having a length less than the thickness of the cuneiform and metatarsal, respectively, can be used to connect the intra-osseous support structure to the bones. In embodiments of the plating system having a bone plate, the bone facing surface of the bone plate can be placed facing a dorsal surface of the cuneiform and a dorsal surface of the metatarsal, spanning a joint therebetween, and the fasteners can extend through apertures defined by the plate.

Embodiments of the invention also include methods of plating a bone, such as with the embodiments of bone plating systems described herein. Note the order of steps as described is only exemplary unless otherwise indicated. In some embodiments, after preparing the surgical area, the method can include the step of forming an opening in a first bone portion and a second bone portion. The opening can be formed from a side of the bone. The opening can be formed generally parallel with a longitudinal axis of the bone, or may be formed at an angle with respect to such longitudinal axis such that it crosses the longitudinal axis. The opening can be formed, e.g., by a saw, drill, mill, box chisel, router, or the like.

The method can also include the steps of placing an intra-osseous support structure in the opening and aligning it in a desired position. In some embodiments, the intra-osseous support structure can be placed generally parallel to a longitudinal axis of the bone (e.g., toward a tension side of the longitudinal axis. In other embodiments, the intra-osseous support structure can be placed at a skewed angle relative to the longitudinal axis of the bone, such that it crosses the longitudinal axis of the bone. In such embodiments, at least a portion of the intra-osseous support structure will reside on a tension side of the longitudinal axis and another portion will reside on a compression side of the longitudinal axis. The method can also include the steps of inserting a first fastener through a first bone portion and engaging the first fastener with the intra-osseous support structure, and inserting a second fastener through a second bone portion and engaging the second fastener with the intra-osseous support structure to secure the plating system to the bone. In some embodiments, the step of placing the intra-osseous support structure in the opening includes placing a stop in apposition to the first bone portion or the second bone portion. In embodiments of intra-osseous support structures having tabs, the method can also include removing the tab after placement of the support structure. Embodiments of the method can also include attaching an additional support structure to the first bone portion and the second bone portion.

In some embodiments, the method can also include the step of forming a first hole in the first bone portion from the first surface and toward an opposite surface and forming a second hole in the second bone portion from the second surface and toward an opposite surface. The first and second holes and the opening can intersect. The first and second holes can be formed, for example, with hand-driven or powered drills. In such embodiments, the fasteners can be inserted through the holes to engage an intra-osseous support structure placed within the opening.

Embodiments of the method also include placing a bone plate having a first portion in apposition to a first surface of a first bone portion and a second portion in apposition to a second surface of a second bone portion, the bone plate having a first aperture in the first portion and a second aperture in the second portion. The bone plate can be initially held in position by pins and/or protrusions. The fasteners can be inserted through apertures defined by the plate.

Thus, embodiments of the invention are disclosed. Although the present invention has been described with reference to certain disclosed embodiments, the disclosed embodiments are presented for purposes of illustration and not limitation, and other embodiments of the invention are possible. One skilled in the art will appreciate that various changes, adaptations, and modifications may be made without departing from the spirit of the invention.

The invention claimed is:

1. A method of plating a bone, comprising the steps of:
    forming an opening in a longitudinal side of a cuneiform and in a longitudinal side of a metatarsal;
    placing an intra-osseous support structure in the opening and across a tarsal-metatarsal joint;
    inserting a first fastener through the cuneiform and into the intra-osseous support structure; and
    inserting a second fastener through the metatarsal and into the intra-osseous support structure.

2. The method of claim 1, further comprising:
    forming a first hole in the cuneiform, the first hole and the opening intersecting; and
    forming a second hole in the metatarsal, the second hole and the opening intersecting,
    wherein the first fastener is inserted through the first hole and the second fastener is inserted through the second hole.

3. The method of claim 1, further comprising:
    placing a bone plate having a first portion in apposition to a first surface of the cuneiform and a second portion in apposition to a second surface of the metatarsal, the bone plate having a first aperture in the first portion and a second aperture in the second portion;
    inserting the first fastener through the first aperture before inserting the first fastener into the cuneiform and into the intra-osseous support structure; and
    inserting the second fastener through the second aperture before inserting the second fastener into the metatarsal and into the intra-osseous support structure.

4. The method of claim 3, wherein the first surface is a dorsal surface of the cuneiform, and the second surface is a dorsal surface of the metatarsal.

5. The method of claim 1, further comprising:
    engaging the first fastener with the intra-osseous support structure; and
    engaging the second fastener with the intra-osseous support structure.

6. The method of claim 1, wherein the cuneiform is a medial cuneiform and the metatarsal is a first metatarsal.

7. The method of claim 1, wherein the opening is located between a dorsal surface and a plantar surface of the cuneiform and a dorsal surface and a plantar surface of the metatarsal.

8. The method of claim 1, wherein the opening is located on a tension side of the cuneiform and the metatarsal.

9. The method of claim 1, further including attaching an additional support structure to the cuneiform and the metatarsal.

10. The method of claim 1, further including removing a tab extending beyond a perimeter edge of the intra-osseous support structure.

11. The method of claim 1, wherein the step of placing the intra-osseous support structure in the opening includes placing a stop in apposition to the cuneiform or the metatarsal.

12. The method of claim 1, wherein the first fastener is inserted through the intra-osseous support structure, and further comprising the step of engaging the first fastener with the cuneiform.

13. The method of claim 1, wherein the opening is a slot formed in a medial side of the cuneiform and a medial side of the metatarsal.

* * * * *